United States Patent [19]
Arlt et al.

[11] 3,960,915

[45] June 1, 1976

[54] PROCESS FOR THE PREPARATION OF ISOPROPENYL ISOCYANATE

[75] Inventors: Dieter Arlt; Josef Bremen, both of Cologne, Germany

[73] Assignee: Bayer Aktiengesellschaft, Leverkusen, Germany

[22] Filed: Oct. 9, 1975

[21] Appl. No.: 621,175

[30] Foreign Application Priority Data

Oct. 23, 1974 Germany.............................. 2450285

[52] U.S. Cl..................... 260/453 P; 260/77.5 CR; 260/240 R
[51] Int. Cl.²......................................... C07C 118/00
[58] Field of Search.................................. 260/453 P

[56] References Cited

UNITED STATES PATENTS

| | | |
|---|---|---|
| 3,480,595 | 11/1969 | Burk, Jr. et al................. 260/453 X |
| 3,507,900 | 4/1970 | Burk, Jr. et al..................... 260/453 |

*Primary Examiner*—Lewis Gotts
*Assistant Examiner*—Dolph H. Torrence
*Attorney, Agent, or Firm*—Joseph C. Gil; Gene Harsh

[57] ABSTRACT

The instant invention is directed to a process for the preparation of isopropenyl isocyanate comprising pyrolyzing 5-isopropenyl-1,3,4-dioxazolinone-2 in the gaseous phase, at a temperature above 200°C.

2 Claims, No Drawings

PROCESS FOR THE PREPARATION OF ISOPROPENYL ISOCYANATE

BACKGROUND OF THE INVENTION

It is known (see e.g. German Offenlegungsschrift No. 1,768,808) that 1,3,4-dioxazolinone-2 which is substituted by alkyl or aryl groups in the 5-position may be decomposed into isocyanates and carbon dioxide by heating to temperatures of from about 100°C to about 200°C in inert solvents. However, if attempts are made to decompose 5-vinyl- or 5-isopropenyl-1,3,4-dioxazolinone-2 into vinyl isocyanate or isopropenylisocyanate and carbon dioxide by the action of heat under the conditions previously known, secondary reactions (in particular, polymerization) occur. Accordingly, isocyanate-containing monomers cannot therefore be prepared in this way.

The unsaturated isocyanates are monomers which may be used in a variety of ways for the production of modified synthetic resins, [Chem. High Polymers Tokyo, 13, 125 (1956); Bull. Soc. Chim. Belge 65, 571 (1956); ibid 66, 229 (1957); Makromol. Chem. 47, 143 (1961), Makromol. Chem. 31, 230 (1959)]. The synthesis previously known, [see e.g. Journal of Organic Chemistry 26, 770–9 (1961), ibid 27, 1454–5 (1962); Chemische Berichte 98, 650–2 (1965)] are not suitable for commercial production since synthesis by way of the corresponding acid azides proceeds by way of dangerous explosive intermediates and requires expensive starting materials, such as methacrylic acid chloride and sodium azide. The problem therefore arises of finding some way of decomposing 5-isopropenyl-1,3,4-dioxazolinone-2 (which as is known may be prepared by a technically satisfactory process from very easily available starting materials, namely methacrylic acid esters, hydroxylamine and phosgene) into the desired isopropenyl isocyanate.

DESCRIPTION OF THE INVENTION

Although experiments carried out under the known conditions led only to polymers and not to isopropenyl isocyanate, it has surprisingly been found that at substantially higher temperatures, pyrolysis of 5-isopropenyl-1,3,4-dioxazolinone-2 results in excellent yields of isopropenyl isocyanate if the pyrolysis is carried out in the gaseous phase.

This invention therefore relates to a process for the preparation of isopropenyl isocyanate comprising pyrolyzing 5-isopropenyl-1,3,4-dioxazolinone-2 in the gaseous phase at a temperature of about 200°C.

The temperatures employed for pyrolysis in the process according to the invention are above 200°C and are generally from about 250° to 500°C and are preferably from 250° to 400°C.

Pyrolysis may be carried out either under vacuum or at normal pressure. The pyrolysis is generally carried out at from about 1 to 760 Torr and preferably from 15 to 760 Torr.

The reaction may be carried out in a reactor of known construction, e.g. a tube reactor, with or without the use of known inert filling materials. Filling bodies made of quartz, glass, aluminum oxide, iron, clay or active charcoal may generally be used to improve the heat transfer.

An inert gas, such as nitrogen, is suitably passed through the reactor as propellant gas.

The products generally leaving the reactor in the gaseous state are subsequently cooled and condensed. The condensate is purified by distillation. Nitrile carbonates of the kind of 5-isopropenyl-1,3,4-dioxazolinone-2 are known compounds which may be prepared following the teaching of U.S. Pat. No. 3,531,425. Another suitable method for preparing 5-isopropenyl-1,3,4-dioxazolinone-2 is as follows.

Preparation of the starting material 5-isopropenyl-1,3,4-dioxazolinone-2

100.1 g (1.0 mol) of methyl methacrylate and approximately 0.5 g of 2,2'-dihydroxy-3,3'-dicyclohexyl-5,5'-dimethyldiphenylmethane are added to a solution of 82.1 g (0.5 mol) of hydroxylammonium sulphate in 250 ml of water at from 0° to 5°C. A solution of 40 g (1.0 mol) of sodium hydroxide in 70 ml of water is added dropwise to this mixture with vigorous stirring. After stirring for one hour, a solution of 40 g (1.0 mol) of sodium hydroxide in 70 ml of water is added dropwise at the above temperature. The reaction mixture is then left to warmup to room temperature over a period of 2 hours and stirred for a further 2 hours.

600 ml of methylene chloride and 0.5 g of phenothiazine are added to the resulting aqueous solution of the sodium salt of methacrylhydroxamic acid. 120 g (1.2 mol) of phosgene are introduced into this mixture at from 0° to 5°C with vigorous stirring and with pH control. As soon as the reaction mixture is at pH 5, a 40% sodium hydroxide solution is added dropwise so that the pH of the mixture is maintained at from pH 4 to pH 6 during further addition of phosgene. Stirring is continued for about one hour after which time all the phosgene has been added. The pH of the mixture is maintained within the given range by further addition of sodium hydroxide solution.

The phases are then separated and the aqueous phase is extracted twice with methylene chloride and the combined organic phases are dried over a zeolite-type having a width of pore of 4 A and a particle size of 3–6 mm. After removal of the solvent by distillation under vacuum, the residue is distilled in an oil pump vacuum.

B.p.$_{0.1}$: 38° – 40°C. M.p.: 34°C. Yield: 108 g $\triangleq$ 85.4% of the theoretical yield The invention is further illustrated but is not intended to be limited by the following examples in which all parts and percentages are by weight unless otherwise specified.

EXAMPLE 1

127 g (1.0 mol) of 5-isopropenyl-1,3,4-dioxazolinone-2 are introduced dropwise at the rate of 50 g/h and at a pyrolysis temperature of 400°C into a pyrolysis tube measuring 60 cm in length and 3 cm in diameter which is filled with Raschig rings 6 mm in diameter. At the same time, nitrogen is passed through the tube at the rate of 8 l/h. The isopropenyl isocyanate discharged from the end of the pyrolysis tube is condensed by chilling to −60°C and the resulting condensated is purified by fractional distillation. Yield: 74 g $\triangleq$ 89% of the theoretical yield.

EXAMPLE 2

127 g (1.0 mol) of 5-isopropenyl-1,3,4-dioxazolinone-2 are introduced dropwise at the rate of 25 g/h and at a pressure of 200 Torr into an evaporator which is heated to 155°C. The evaporated product is introduced into the pyrolysis reactor described in Example 1 at a pyrolysis temperature of 400°C and at a pressure of 200 Torr. The gaseous mixture leaving the end of the pyrolysis tube is condensed by chilling to −60°C and the resulting condensate is purified by distillation. Yield: 70.5 g ≙ 85% of the theoretical yield.

COMPARISON EXAMPLE (corresponding to German Offenlegungsschrift No. 1,768,808)

50 g (0.394 mol) of 5-isopropenyl-1,3,4-dioxoazolinone-2 and 400 ml of o-dichlorobenzene are mixed and heated under reflux with stirring until evolution of $CO_2$ ceases. The reaction time is approximately 6 hours. Fractional distillation of the resulting solution is then attempted. No isopropenyl isocyanate is obtained.

What is claimed is:

1. A process for the preparation of isopropenyl isocyanate comprising pyrolyzing 5-isopropenyl-1,3,4-dioxazolinone-2 in the gaseous phase at a temperature of above 200°C.

2. The process of claim 1 wherein the pyrolysis temperature is from 250° to 500°C.

* * * * *